United States Patent
Onogi et al.

(10) Patent No.: US 9,140,202 B2
(45) Date of Patent: Sep. 22, 2015

(54) SENSOR CONTROL DEVICE, SENSOR CONTROL METHOD AND COMPUTER READABLE RECORDING MEDIUM

(71) Applicant: NGK SPARK PLUG CO., LTD., Nagoya-shi, Aichi (JP)

(72) Inventors: Hirotaka Onogi, Kakamigahara (JP); Kenji Kato, Nagoya (JP); Kouichi Imaeda, Kounan (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 167 days.

(21) Appl. No.: 13/938,738

(22) Filed: Jul. 10, 2013

(65) Prior Publication Data
US 2014/0014535 A1    Jan. 16, 2014

(30) Foreign Application Priority Data
Jul. 13, 2012    (JP) .................................. 2012-157430

(51) Int. Cl.
G01N 27/419    (2006.01)
F02D 41/14    (2006.01)
G01N 27/407    (2006.01)
G01N 33/00    (2006.01)

(52) U.S. Cl.
CPC ............ *F02D 41/146* (2013.01); *G01N 27/407* (2013.01); *G01N 27/419* (2013.01); *G01N 33/0037* (2013.01); *F02D 41/1474* (2013.01); *Y02T 10/42* (2013.01)

(58) Field of Classification Search
CPC ............. G01N 27/404–27/407; G01N 27/409; G01N 27/419; G01N 27/41; G01N 1/2252; G01M 15/10; G01M 15/102; G01M 15/104; F01N 2560/00; F01N 2550/00; F01N 3/10; F01N 11/00
See application file for complete search history.

(56) References Cited

U.S. PATENT DOCUMENTS

2011/0132775 A1*    6/2011    Kawai et al. ................... 205/784

FOREIGN PATENT DOCUMENTS

JP    2011-137806 A    7/2011

* cited by examiner

*Primary Examiner* — Jennifer Dieterle
(74) *Attorney, Agent, or Firm* — Sughrue Mion, PLLC

(57) ABSTRACT

In a sensor control device, it is determined whether a gas sensor is activated. A concentration control is performed at an elapse timing which elapses by a first constant time from an activation timing at which the gas sensor is determined to be activated. A preliminary control is performed in at least a partial period between the elapse timing and a start timing at which a drive control is started.

5 Claims, 6 Drawing Sheets

SENSOR CONTROL DEVICE, SENSOR CONTROL METHOD AND COMPUTER READABLE RECORDING MEDIUM

CROSS REFERENCE TO RELATED APPLICATION

This application is based upon and claims the benefit of priority of Japanese Patent Application No. 2012-157430 filed on Jul. 13, 2012, the contents of which are incorporated herein by reference in its entirety.

BACKGROUND

The present invention relates to a sensor control device that calculates a concentration correspondence value indicating a concentration of a specific gas included in a detection target gas, a sensor control method and a computer readable recording medium storing a program for the sensor control device.

Conventionally, a gas sensor has been used which detects a concentration of a specific gas included in a detection target gas such as an exhaust gas. For example, an $NO_x$ sensor detecting nitrogen oxide (hereinafter, referred to as "$NO_x$") as a specific gas includes an oxygen concentration detecting cell, a first oxygen pump cell, and a second oxygen pump cell. These cells comprise of a solid electrolyte layer having oxygen ion conductivity and a pair of electrodes, respectively. The $NO_x$ sensor pumps oxygen out of a first measuring chamber by the use of the first oxygen pump cell to keep the oxygen concentration of the detection target gas in the first measuring chamber constant so that the output voltage of the oxygen concentration detecting cell is constant. The $NO_x$ sensor applies an operation voltage between the electrodes of the second oxygen pump cell to pump oxygen out of the gas (the gas of which the oxygen concentration is adjusted by the first oxygen pump cell) introduced into the second measuring chamber from the first measuring chamber by the use of the second oxygen pump cell. The $NO_x$ concentration in the detection target gas is detected based on the value of current flowing in the second oxygen pump cell by application of the operation voltage (hereinafter, a process of detecting the $NO_x$ concentration in the detection target gas is referred to as a "detection process").

For example, when an $NO_x$ concentration in an exhaust gas discharged from an internal combustion engine of an automobile is detected using an $NO_x$ sensor, the gas present in the second measuring chamber is in a lean state similar to the atmospheric air according to the elapsed time since the previous operation of the internal combustion engine restarts up after it stops. Accordingly, in the $NO_x$ sensor, the time until the $NO_x$ concentration in the exhaust gas can be stably measured is shortened by performing a preliminary control of temporarily and rapidly pumping out oxygen present in the second measuring chamber or oxygen included in the porous electrode in contact with the second measuring chamber to change the inside of the second measuring chamber to a predetermined state with a low oxygen concentration. For example, in a sensor control device described in JP-A-2011-137806, as the preliminary control, constant current is supplied to the second oxygen pump cell for a constant time under the control condition determined for each gas sensor after gas sensors are started up to temporarily and rapidly pump out oxygen present in the second measuring chamber. In the sensor control device described in Patent JP-A-2011-137806, even when an $H_2O$ concentration of the detection target gas varies for every startup of the sensor control device or even when the gas sensor has a deviation in output characteristics, the temporal variation in concentration correspondence value calculated after the preliminary control ends can be made to substantially maintain the same pattern.

SUMMARY

In the sensor control device described in JP-A-2011-137806, the control condition of the preliminary control is determined on the premise that the gas present in the second measuring chamber before performing the preliminary control is in a lean state similar to the atmospheric air. However, the inventors of the present invention found a problem that the oxygen concentration in the gas, which is present in the second measuring chamber just before performing the preliminary control, may be lower than the oxygen concentration of the atmospheric air. In this case, when the conventional preliminary control is performed, the gas sensor pumps out a larger amount of oxygen present in the second measuring chamber than an assumed amount and performs the preliminary control, whereby the inside of the second measuring chamber is not in the predetermined state with a low oxygen concentration. As a result, a relatively long time is taken until the concentration correspondence value calculated after the preliminary control exhibits a normal value. Therefore, the conventional sensor control device cannot stably detect a concentration of a specific gas early.

This problem is not a problem limited to the $NO_x$ sensor elements detecting the $NO_x$ concentration correspondence value but a problem occurring in a gas sensor detecting concentrations of various specific gases using an oxygen pump cell.

An object is to provide a sensor control device which enables stable detection of a concentration of a specific gas early.

One of aspects of the present invention provides the following arrangements:

A sensor control device comprising:
a gas sensor including:
a first measuring chamber into which a detection target gas is to be introduced;
a first oxygen pump cell that includes a first solid electrolyte layer and a pair of first electrodes which are disposed inside and outside the first measuring chamber, respectively;
a second measuring chamber communicating with the first measuring chamber; and
a second oxygen pump cell that includes a second solid electrolyte layer and a pair of second electrodes which are disposed inside and outside the second measuring chamber, respectively; and
a controller configured to:
perform a concentration control of adjusting an oxygen concentration in the detection target gas introduced into the first measuring chamber to a predetermined value through electrification of the first oxygen pump cell;
perform a drive control of applying an operation voltage to the second oxygen pump cell;
calculate a concentration correspondence value indicating a concentration of a specific gas based on the magnitude of current flowing in the second oxygen pump cell to which the operation voltage has been applied;
determine whether the gas sensor is activated;
perform a preliminary control of lowering the oxygen concentration in the second measuring chamber before starting the drive control;

perform the concentration control at an elapse timing which elapses by a first time from an activation timing at which the gas sensor is determined to be activated; and perform the preliminary control in at least a partial period between the elapse timing and a start timing at which the drive control is started.

A sensor control method for controlling a gas sensor including: a first measuring chamber into which a detection target gas is to be introduced; a first oxygen pump cell that includes a first solid electrolyte layer and a pair of first electrodes which are disposed inside and outside the first measuring chamber, respectively; a second measuring chamber communicating with the first measuring chamber; and a second oxygen pump cell that includes a second solid electrolyte layer and a pair of second electrodes which are disposed inside and outside the second measuring chamber, respectively, the sensor control method comprising:

performing a concentration control of adjusting an oxygen concentration in the detection target gas introduced into the first measuring chamber to a predetermined value through electrification of the first oxygen pump cell;

performing a drive control of applying an operation voltage to the second oxygen pump cell;

calculating a concentration correspondence value indicating a concentration of a specific gas based on the magnitude of current flowing in the second oxygen pump cell to which the operation voltage has been applied;

determining whether the gas sensor is activated;

performing a preliminary control of lowering the oxygen concentration in the second measuring chamber before starting the drive control;

performing the concentration control at an elapse timing which elapses by a first time from an activation timing at which the gas sensor is determined to be activated; and performing the preliminary control in at least a partial period between the elapse timing and a start timing at which the drive control is started.

A non-transitory computer readable recording medium storing a program, for a sensor control device including: a first measuring chamber into which a detection target gas is to be introduced; a first oxygen pump cell that includes a first solid electrolyte layer and a pair of first electrodes which are disposed inside and outside the first measuring chamber, respectively; a second measuring chamber communicating with the first measuring chamber; and a second oxygen pump cell that includes a second solid electrolyte layer and a pair of second electrodes which are disposed inside and outside the second measuring chamber, respectively, the program when executed by a processor causing the sensor control device to:

perform a concentration control of adjusting an oxygen concentration in the detection target gas introduced into the first measuring chamber to a predetermined value through electrification of the first oxygen pump cell;

perform a drive control of applying an operation voltage to the second oxygen pump cell;

calculate a concentration correspondence value indicating a concentration of a specific gas based on the magnitude of current flowing in the second oxygen pump cell to which the operation voltage has been applied;

determine whether the gas sensor is activated;

perform a preliminary control of lowering the oxygen concentration in the second measuring chamber before starting the drive control;

perform the concentration control at an elapse timing which elapses by a first time from an activation timing at which the gas sensor is determined to be activated; and perform the preliminary control in at least a partial period between the elapse timing and a start timing at which the drive control is started.

The reasons for the problem that the oxygen concentration of the gas present in the second measuring chamber just before performing the preliminary control is smaller than the oxygen concentration in the atmospheric air have been studied by the inventors of the present invention and two reasons have been considered. The first reason is that an unburned material enters the gas sensor. Examples of the unburned material include a fuel such as gasoline, components included in a coating material (for example, a baking inhibitor for preventing the outer circumference of a housing of the gas sensor from sticking to a mounting section disposed in an exhaust passage) applied to the gas sensor, and components included in a packaging material used to store the gas sensor. When an unburned material enters the gas sensor, the unburned material is oxidized in the course of activating the gas sensor, thereby consuming oxygen in the gas sensor. Accordingly, the oxygen concentration of the gas present in the second measuring chamber just before performing the preliminary control is smaller than the oxygen concentration of the atmospheric air. The second reason is that the time taken for replacing the gas in the second measuring chamber is not sufficiently guaranteed after the gas sensor is activated. When the gas sensor is not activated, the oxygen pumping performance of the second oxygen pump cell is not stabilized and thus the preliminary control is performed after the activation timing at which the gas sensor is determined to be activated. However, the preliminary control may be started from the activation timing. This is intended to make the time (hereinafter, also referred to as "startup time"), which is taken until a concentration correspondence value of a specific gas can be stably measured after the gas sensor is started up, as short as possible. In the preliminary control, the oxygen concentration in the first measuring chamber supplying the gas to the second measuring chamber is also simultaneously lowered in order to lower the oxygen concentration in the second measuring chamber to a predetermined low concentration for a short time. Therefore, when the preliminary control is first started, the oxygen concentration of the gas present in the second measuring chamber does not reach the oxygen concentration of the atmospheric air. In this way, since the timing at which the preliminary control is started is not set in consideration of the problem that the oxygen concentration of the gas, which is present in the second measuring chamber just before performing the preliminary control, may be lower than the oxygen concentration of the atmospheric air, the time taken for replacing the gas in the second measuring chamber with the atmospheric air is not sufficiently guaranteed.

In consideration of the two reasons, the sensor control device according to this aspect performs a concentration control from an elapse timing and performs a preliminary control in at least a partial period between the elapse timing and the start timing. The elapse timing is a timing at which a first time elapses from the activation timing. The sensor control device according to this aspect can guarantee the time taken for replacing the atmosphere of the second measuring chamber with the ambient atmosphere of the gas sensor under the condition in which the gas sensor is activated, by setting the timing for performing the preliminary control to a timing after the elapse timing. Therefore, the sensor control device according to this aspect can enable stable detection of a concentration of a specific gas early without depending on whether an unburned material enters the gas sensor, by raising the possibility that the atmosphere of the second measuring chamber before starting the preliminary control will be an atmosphere similar to the atmospheric air.

When the voltage value applied to the second oxygen pump cell is equal to or greater than a predetermined value, the magnitude of current flowing between the second electrodes of the second oxygen pump cell increases in proportion to the $H_2O$ concentration included in the detection target gas. Accordingly, even when the same voltage is applied to the second oxygen pump cell, the amount of oxygen pumped out by the second oxygen pump cell varies depending on the $H_2O$ concentration of the detection target gas. On the contrary, in the sensor control device according to this aspect, the preliminary control means may perform the preliminary control by supplying constant current to the second oxygen pump cell for a constant second time and controlling the amount of oxygen pumped out from the second measuring chamber to the outside of the second measuring chamber so as to be constant. In this case, in the sensor control device, since the amount of oxygen pumped out by the second oxygen pump cell is proportional to the value of current flowing between a pair of second electrodes of the second oxygen pump cell, the oxygen concentration in the second measuring chamber is substantially constant without depending on the $H_2O$ concentration included in the detection target gas. Therefore, the temporal variation of the concentration correspondence value calculated after ending the preliminary control exhibits substantially the same pattern even when the $H_2O$ concentration in the detection target gas varies for every performance of the drive control. That is, in the sensor control device in this case, even when the $H_2O$ concentration in the detection target gas varies, it is possible to reduce the deviation of the concentration correspondence value for every performance of the drive control after starting the drive control.

The preliminary control in this aspect is performed at any timing between the elapse timing which elapses by the first time from the activation timing and the start timing. Accordingly, the startup time increases according to the magnitude of the first time. On the contrary, in the sensor control device according to this aspect, the first time may be shorter than the second time. In the sensor control device in this case, it is possible to stably detect the concentration of a specific gas early while suppressing the ratio at which the first time occupies the startup time so as to be low, by setting the first time to be shorter than the second time.

DESCRIPTION OF EXEMPLARY EMBODIMENTS

Hereinafter, sensor control devices according to first and second embodiments of the present invention will be sequentially described with reference to the accompanying drawings. The drawings to be referred to are used to explain technical features which can be employed by the present invention, and configurations of the devices described herein are not intended to limit the present invention but are only simple explanation examples.

Figure 1:
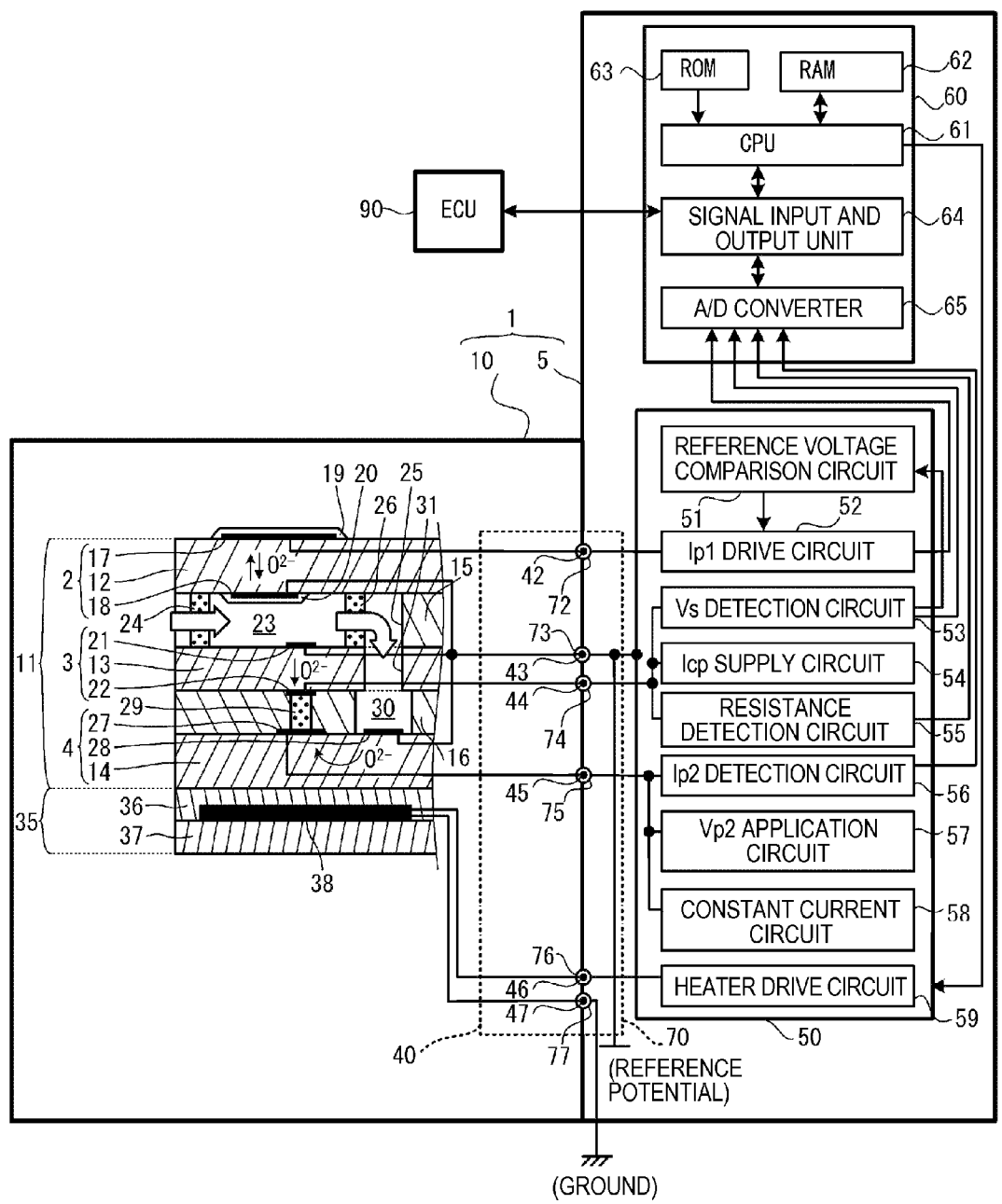
FIG. 1 is a conceptual diagram of a sensor control device 1 according to a first embodiment.

A sensor control device 1 has a function of detecting a concentration of nitrogen oxide ($NO_x$) as a specific gas. As shown in FIG. 1, the sensor control device 1 includes a gas sensor 10 and a controller 5. The gas sensor 10 is mounted on an exhaust passage (not shown) of an automobile and outputs a current value corresponding to the $NO_x$ concentration in the exhaust gas to the controller 5. The controller 5 is electrically connected to the gas sensor 10 to control the gas sensor 10 and calculates a concentration correspondence value (hereinafter, referred to as an "$NO_x$ concentration correspondence value") indicating the $NO_x$ concentration in the exhaust gas based on the current value output from the gas sensor 10. The controller 5 according to this embodiment calculates the $NO_x$ concentration as the $NO_x$ concentration correspondence value. The gas sensor 10 and the controller 5 of the sensor control device 1 will be described below in detail.

The gas sensor 10 includes a detection element 11, a heater element 35, a connector section 40, and a housing (not shown). The detection element 11 is formed in a layered shape in which insulators 15 and 16 formed of alumina or the like are interposed between three plate-like solid electrolytes 12, 13, and 14. The heater element 35 is stacked on the solid electrolyte 14 for the purpose of early activation of the solid electrolytes 12 to 14 and maintaining of activation stability of the solid electrolytes 12 to 14. The connector section 40 is connected to the detection element 11 and the heater element 35 via lead lines and is disposed to electrically connect the gas sensor 10 and the controller 5 to each other. The housing holds the detection element 11 and the heat element 35 therein so as to mount the gas sensor 10 in the exhaust passage (not shown). The constituents of the gas sensor 10 will be described below in detail.

First, the configuration of the detection element 11 will be described. The detection element 11 includes a first measuring chamber 23, a second measuring chamber 30, a reference oxygen chamber 29, a first oxygen pump cell 2 (hereinafter, referred to as "Ip1 cell 2"), an oxygen partial pressure detecting cell 3 (hereinafter, referred to as a "Vs cell 3"), and a second oxygen pump cell 4 (hereinafter, referred to as an "Ip2 cell 4").

The first measuring chamber 23 is a small space at which the exhaust gas in the exhaust passage is first introduced into the detection element 11. The first measuring chamber 23 is formed between the solid electrolyte 12 and the solid electrolyte 13. An electrode 18 is disposed on the surface of the first measuring chamber 23 facing the solid electrolyte 12, and an electrode 21 is disposed on the surface facing the solid electrolyte 13. A porous first diffusion resisting portion 24 is disposed on the front side of the detection element 11 in the first measuring chamber 23. The first diffusion resisting portion 24 serves as a partition between the inside and the outside of the first measuring chamber 23 and limits the flow per unit time of the exhaust gas into the first measuring chamber 23. Similarly, a porous second diffusion resisting portion 26 is disposed on the rear side of the detection element 11 in the first measuring chamber 23. The second diffusion resisting portion 26 serves as a partition between the first measuring chamber 23 and the second measuring chamber 30 and limits the flow per unit time of the gas into the second measuring chamber 30 from the first measuring chamber 23.

The second measuring chamber 30 is a small space surrounded with the solid electrolyte 12, the second diffusion resisting portion 26, the opening 25, the opening 31 formed in the solid electrolyte 13, the insulator 16, and the electrode 28. The second measuring chamber 30 communicates with the first measuring chamber 23 and the exhaust gas (hereinafter, referred to as an "adjusted gas") of which the oxygen concentration is adjusted by the Ip1 cell 2 is introduced therein. The reference oxygen chamber 29 is a small space surrounded with the insulator 16, the electrode 22, and the electrode 27. The reference oxygen chamber 29 is filled with a porous material formed of ceramic.

The Ip1 cell 2 includes the solid electrolyte 12 and the porous electrodes 17 and 18. The solid electrolyte 12 is formed of, for example, zirconia and has oxygen ion conductivity. The electrodes 17 and 18 are disposed on both surfaces of the solid electrolyte 12 in the stacking direction of the detection element 11, respectively. The electrodes 17 and 18 are formed of material containing Pt as a major component. Examples of the material containing Pt as a major component include Pt, Pt alloy, and cermet containing Pt and ceramic. Porous protective layers 19 and 20 formed of ceramic are formed on the surfaces of the electrodes 17 and 18, respectively. The solid electrolyte 12 corresponds to the "first solid electrolyte layer" in the present invention and the electrodes 17 and 18 correspond to a "pair of first electrodes" in the present invention.

The Ip1 cell 2 performs pumping out and pumping in (so-called oxygen pumping) of oxygen between the atmosphere (the atmosphere outside the detection element 11) in contact with the electrode 17 and the atmosphere (the atmosphere inside the first measuring chamber 23) in contact with the electrode 18 by supplying current between both electrodes 17 and 18.

The Vs cell 3 includes the solid electrolyte 13 and the porous electrodes 21 and 22. The solid electrolyte 13 is formed of, for example, zirconia and has oxygen ion conductivity. The solid electrolyte 13 is disposed to face the solid electrolyte 12 with the insulator 15 interposed therebetween. The electrodes 21 and 22 are disposed on both surfaces of the solid electrolyte 13 in the stacking direction of the detection element 11, respectively. The electrode 21 is formed on the surface of the first measuring chamber 23 facing the solid electrolyte 12. The electrodes 21 and 22 are formed of the above-mentioned material containing Pt as a major component.

The Vs cell 3 generates an electromotive force mainly depending on the oxygen partial pressure difference between the atmospheres (the atmosphere inside the first measuring chamber 23 in contact with the electrode 21 and the atmosphere inside the reference oxygen chamber 29 in contact with the electrode 22) separated from each other by the solid electrolyte 13.

The Ip2 cell 4 includes the slid electrolyte 14 and the porous electrodes 27 and 28. The solid electrolyte 14 is formed of, for example, zirconia and has oxygen ion conductivity. The solid electrolyte 14 is disposed to face the solid electrolyte 13 with the insulator 16 interposed therebetween. The electrodes 27 and 28 formed of the above-mentioned material containing Pt as a major component are formed on the surface of the solid electrolyte 14 facing the solid electrolyte 13. The solid electrolyte 14 corresponds to the "second solid electrolyte layer" in the present invention and the electrodes 27 and 28 correspond to the "pair of second electrodes" in the present invention.

The Ip2 cell 4 pumps out oxygen between the atmospheres (the atmosphere inside the reference oxygen chamber 29 in contact with the electrode 27 and the atmosphere inside the second measuring chamber 30 in contact with the electrode 28) separated from each other by the insulator 16.

The heater element 35 will be described below. The heater element 35 includes insulating layers 36 and 37 and a heater pattern 38. The insulating layers 36 and 37 have a sheet-like shape containing alumina as a major component. The heater patter 38 is embedded between the insulating layers 36 and 37 and is a single electrode pattern connected in the heater element 35. One end of the heater pattern 38 is grounded and the other end is connected to a heater drive circuit 59. The heater pattern 38 is formed of a material containing Pt as a major component.

The connector section 40 will be described below. The connector section 40 is disposed on the rear side of the gas sensor 10 and includes terminals 42 to 47. The electrode 17 is electrically connected to the terminal 42 via a lead line. The electrode 18, the electrode 21, and the electrode 28 are electrically connected to the terminal 43 at the same potential via lead lines. The electrode 22 is electrically connected to the terminal 44 via a lead line. The electrode 27 is electrically connected to the terminal 45 via a lead line. The heater pattern 38 is electrically connected to the terminals 46 and 47 via lead lines.

The configuration of the controller 5 will be described below. The controller 5 is a unit that controls the detection element 11 and the heater element 35, that calculates a $NO_x$ concentration correspondence value based on the current Ip2 acquired from the detection element 11, and that outputs the calculated $NO_x$ concentration correspondence value to an ECU 90. The controller 5 includes a drive circuit unit 50, a micro computer 60, and a connector section 70. The drive circuit unit 50 controls the detection element 11 and the heater element 35. The micro computer 60 controls the drive circuit unit 50. The connector section 70 is electrically connected to the connector section 40 of the gas sensor 10. The constituents of the controller 5 will be described below.

The drive circuit unit 50 includes a reference voltage comparison circuit 51, an Ip1 drive circuit 52, a Vs detection circuit 53, an Icp supply circuit 54, a resistance detection circuit 55, an Ip2 detection circuit 56, a Vp2 application circuit 57, a constant current circuit 58, and a heater drive circuit 59. The circuits are driven in accordance with control signals from the micro computer 60. The constituents of the drive circuit unit 50 will be described below in detail.

The Icp supply circuit 54 supplies weak current Icp between the electrodes 21 and 22 of the Vs cell 3 and pumps out oxygen from the first measuring chamber 23 to the reference oxygen chamber 29. The Vs detection circuit 53 is a circuit for detecting a voltage (an electromotive force) Vs between the electrodes 21 and 22 and outputs the detection result to the reference voltage comparison circuit 51. The reference voltage comparison circuit 51 is a circuit for comparing the voltage Vs detected by the Vs detection circuit 53 with a reference voltage as a reference (for example, 425 mV) and outputs the comparison result to the Ip1 drive circuit 52.

The Ip1 drive circuit 52 is a circuit for supplying current Ip1 between the electrodes 17 and 18 of the Ip1 cell 2. The Ip1 drive circuit 52 adjusts the magnitude or direction of the current Ip1 so that the voltage Vs is substantially equal to a predetermined reference voltage based on the comparison result of the voltage Vs between the electrodes 21 and 22 of the Vs cell 3 by the reference voltage comparison circuit 51. As a result, the Ip1 cell 2 pumps out oxygen from the first measuring chamber 23 to the outside of the detection element 11 or pumps oxygen into the first measuring chamber 23 from the outside of the detection element 11. In other words, the Ip1 cell 2 adjusts the oxygen concentration in the first measuring chamber 23 so that the voltage between the electrodes 21 and 22 of the Vs cell 3 is maintained at a constant value (the value of the reference voltage) based on the control of electrification by the Ip1 drive circuit 52.

The resistance detection circuit 55 is a circuit for periodically supplying current having a predetermined value to the Vs cell 3 in a pulse shape and detecting a voltage variation (variation of the voltage Vs) acquired in response to the supply of current. The value indicating the voltage variation detected by the resistance detection circuit 55 is output to the micro computer 60, and an internal resistance (impedance) Rpvs of the Vs cell 3 is obtained based on the table in which the variation of the voltage Vs and the internal resistance Rpvs of the Vs cell 3 are correlated in advance and which is stored in the micro computer 60. The internal resistance Rpvs of the Vs cell 3 has a correlation with the temperature of the Vs cell 3, that is, the whole temperature of the detection element 11. The micro computer 60 detects the temperature of the detection element 11 based on the internal resistance Rpvs of the Vs cell 3. The circuit configuration of the resistance detection circuit 55 for detecting the voltage variation indicating the internal resistance Rpvs of the Vs cell 3 is known, for example, in JP-A-11-307458 and thus description thereof will not be repeated any more.

The Ip2 detection circuit 56 is a circuit for detecting the value of current Ip2 flowing between the electrodes 27 and 28 of the Ip2 cell 4. The Vp2 application circuit 57 is a circuit for applying an operation voltage Vp2 (for example, 450 mV) between the electrodes 27 and 28 of the Ip2 cell 4 at the time of performing a drive control process to be described later, and controls pumping out of oxygen from the inside of the second measuring chamber 30 to the reference oxygen chamber 29. The constant current circuit 58 is a circuit for supplying current Ip3 (for example, 10 μA) having a constant value between the electrode 28 and the electrode 27 of the Ip2 cell 4 at the time of performing a preliminary control process to be described later.

The heater drive circuit 59 is a circuit for maintaining the temperature (the temperature of the gas sensor 10) of the solid electrolytes 12, 13, and 14 at a predetermined temperature. The heater drive circuit 59 is controlled by the micro computer 60 and heats the solid electrolytes 12, 13, and 14 (in other words, the Ip1 cell 2, the Vs cell 3, and the Ip2 cell 4) by causing current to flow to the heater pattern 38 of the heater element 35. The heater drive circuit 59 can perform a control of PWM-electrifying the heater pattern 38 to supply current to the heater pattern 38 so that the solid electrolytes 12, 13 and 14 (specifically the Vs cell 3) reaches a target heating temperature.

The micro computer 60 is a computing device including a CPU 61, a ROM 63, a RAM 62, a signal input and output unit 64, and an A/D converter 65, which are known well. The micro computer 60 outputs control signals to the drive circuit unit 50 in accordance with a program installed in advance therein to control the operations of the circuits of the drive circuit unit 50. The ROM 63 stores various programs and various parameters referred to in executing the programs. The micro computer 60 communicates with the ECU 90 taking charge of control of an internal combustion engine (not shown) via the signal input and output unit 64.

The connector section 70 includes terminals 72 to 77. When the connector section 70 is connected to the connector section 40, the terminals 72 to 77 are connected to the terminals 42 to 47. The Ip1 drive circuit 52 is connected to the terminal 72 via a wire. The terminal 73 is connected to a reference potential via a wire. The Vs detection circuit 53, the Icp supply circuit 54, and the resistance detection circuit 55 are connected to the terminal 74 via wires. The Ip2 detection circuit 56, the Vp2 application circuit 57, and the constant current circuit 58 are connected to the terminal 75 via wires. The heater drive circuit 59 is connected to the terminal 76 via a wire. The terminal 77 is grounded via a wire.

The operation of the sensor control device 1 when the NOx concentration is detected will be described below. The exhaust gas flowing in the exhaust passage (not shown) is introduced into the first measuring chamber 23 via the first diffusion resisting portion 24. Here, in the Vs cell 3, weak current Icp is supplied from the electrode 22 to the electrode 21 by the Icp supply circuit 54. Accordingly, oxygen in the exhaust gas becomes oxygen ions by the electrode 21 as a negative electrode, flows in the solid electrolyte 13, and moves into the reference oxygen chamber 29. That is, oxygen in the first measuring chamber 23 moves to the reference oxygen chamber 29 by supplying the current Icp between the electrodes 21 and 22.

In the Vs detection circuit 53, the voltage Vs between the electrodes 21 and 22 is detected. The detected voltage Vs is compared with the reference voltage (for example, 425 mV) by the reference voltage comparison circuit 51 and the comparison result is output to the Ip1 drive circuit 52. Here, when the oxygen concentration in the first measuring chamber 23 is adjusted so that the potential difference between the electrodes 21 and 22 is constant in the vicinity of the reference voltage, the oxygen concentration in the exhaust gas in the first measuring chamber 23 gets close to a predetermined concentration C (for example, 0.001 ppm).

Therefore, in the Ip1 drive circuit 52, when the oxygen concentration of the exhaust gas introduced into the first measuring chamber 23 is lower than the concentration C, the current Ip1 is supplied to the Ip1 cell 2 so that the electrode 17 serves as the negative electrode. As a result, in the Ip1 cell 2, oxygen is pumped from the outside of the detection element 11 to the inside of the first measuring chamber 23. On the other hand, when the oxygen concentration of the exhaust gas introduced into the first measuring chamber 23 is higher than the concentration C, the Ip1 drive circuit 52 supplies the current Ip1 to the Ip1 cell 2 so that the electrode 18 serves as the negative electrode. As a result, in the Ip1 cell 2, oxygen is pumped from the inside of the first measuring chamber 23 to the outside of the detection element 11. The oxygen concentration in the exhaust gas can be detected based on the magnitude of the current Ip1 and the direction in which the current Ip1 flows.

The adjusted gas of which the oxygen concentration is adjusted to the concentration C in the first measuring chamber 23 is introduced into the second measuring chamber 30 via the second diffusion resisting portion 26. $NO_x$ in the adjusted gas coming in contact with the electrode 28 in the second measuring chamber 30 is decomposed (reduced) into $N_2$ and $O_2$ with the electrode 28 as a catalyst. The decomposed oxygen receives electrons from the electrode 28 and becomes oxygen ions (is dissociated), oxygen ions flow in the solid electrolyte 14 and move into the reference oxygen chamber 29. At this time, the value of current Ip2 flowing between a pair of electrodes 27 and 28 via the solid electrolyte 14 corresponds to the $NO_x$ concentration and the value of the current Ip2 is used to calculate the $NO_x$ concentration correspondence value.

A main process according to the first embodiment shown in FIG. 2 will be described below in brief. In the main process according to the first embodiment, processes including an activation process (the process in a two-dot chained line 91), a preliminary control process (the process in a two-dot chained line 92), a drive control process (the process in a two-dot chained line 93), and a concentration control process (the process in a two-dot chained line 94) are performed. The activation process is a process of heating the detection element 11 by the use of the heater element 35 to activate the detection element 11. The control state of the sensor control device 1 when the activation process is performed is called activation control. The preliminary control process is a process of pumping out a predetermined amount of oxygen in the gas in the second measuring chamber 30 before performing the drive control process. The control state of the sensor control device 1 when the preliminary control process is performed is called preliminary control. The drive control process is a process of applying the operation voltage Vp2 to the Ip2 cell 4. In the drive control process, a process of calculating the $NO_x$ concentration correspondence value is performed based on the magnitude of the current in the Ip2 cell 4 having the operation voltage Vp2 applied thereto. The control state of the sensor control device 1 when the drive control process is performed is called drive control. The concentration control process is a process of adjusting the oxygen concentration of the exhaust gas introduced into the first measuring chamber 23 by electrification of the Ip1 cell 2. The control state of the sensor control device 1 when the concentration control process is performed is called concentration control.

The gas filled in the second measuring chamber 30 at the time of starting up (hereinafter, also referred to as a "startup timing") of the gas sensor 10 is in a lean atmosphere at the time of the present startup after the operation of the internal combustion engine is stopped, that is, after the supply of the exhaust gas is stopped, at the time of performing the previous main process. When the preliminary control is not performed, residual oxygen included in the gas filled in the second measuring chamber 30 before starting the process is pumped out from the second measuring chamber 30 just after starting the drive control process. In this case, the current Ip2 flows which greatly varies depending on the residual oxygen regardless of the $NO_x$ concentration in the exhaust gas to be originally calculated. Therefore, just after starting the drive control process, the $NO_x$ concentration correspondence value based on the current Ip2 does not indicate the value corresponding to the $NO_x$ concentration in the original exhaust gas.

Therefore, the sensor control device 1 according to the first embodiment performs the preliminary control process before performing the drive control process and lowers the oxygen concentration in the second measuring chamber 30 from the lean state. However, when a constant voltage equal to or more than a predetermined value is applied to the Ip2 cell 4, the amount of oxygen to be pumped out by the Ip2 cell 4 differs depending on the $H_2O$ concentration in the gas in the second measuring chamber 30. Therefore, in the first embodiment, the current supplied to the Ip2 cell 4 is controlled to be constant by driving the constant current circuit 58 at the time of performing the preliminary control process. Accordingly, substantially the same amount of oxygen can be pumped out of the second measuring chamber 30 through the preliminary control process when the same gas sensor 10 is used. In the first embodiment, the constant current Ip3 supplied to the Ip2 cell 4 at the time of performing the preliminary control is set to 10 µA. At this time, the voltage applied to the Ip2 cell 4 is larger than the operation voltage Vp2 (for example, 425 mV) which is the voltage at the time of performing the drive control. Accordingly, the amount of oxygen pumped out per unit time at the time of performing the preliminary control is larger than that at the time of performing the drive control.

Gas sensors 10 having the same structure may have different output characteristics. Therefore, when the same control condition is set for different gas sensors 10, the temporal variation of the $NO_x$ concentration correspondence value just after starting the drive control process may differs depending on the gas sensors 10. Accordingly, in the first embodiment, a second time which is a constant electrification time is set for each gas sensor 10 so that the $NO_x$ concentration correspondence value calculated after starting the drive control process (in other words, after ending the preliminary control) is within a target range. The method of setting the second time for each gas sensor 10 is, for example, the same as described in JP-A-2011-137806.

Here, for the reasons such as entrance of an unburned material such as gasoline into the gas sensor 10, the gas filled in the second measuring chamber 30 just after performing the activation process may not be an atmosphere similar to the atmospheric air. Therefore, the sensor control device 1 according to the first embodiment performs the preliminary control in at least a partial period between an elapse timing and a start timing. The elapse timing is a timing which elapses by a constant first time from the activation timing at which the gas sensor is determined to be activated. The start timing is a timing at which the drive control is started. By employing this configuration, the sensor control device 1 guarantees the time taken for replacing the atmosphere of the second measuring chamber with the atmosphere around the gas sensor under the condition that the gas sensor 10 is activated. The first time is set in consideration of the type and the amount of the assumed unburned material, the flow rate of the gas around the gas sensor 10, the size of the second measuring chamber 30, the activation temperature of the gas sensor 10, and the time from the startup timing to the activation timing. The startup time increases in proportion to the length of the first time. Accordingly, the first time is preferably shorter than the second time. More specifically, when the second time is any value in a range of 15 seconds to 30 seconds, the first time is preferably a value smaller than the second time in a range of 5 seconds to 15 seconds. In this case, by setting the first time to a time shorter than the second time, the sensor control device can stably detect the concentration of a specific gas early without depending on whether an unburned material enters the gas sensor while suppressing the ratio of the first time to the startup time to be low.

The main process according to the first embodiment will be described below with reference to FIG. 2. The main process is performed by the CPU 61 of the controller 5 in response to an instruction from the ECU 90 at the time of starting up the internal combustion engine (not shown). The NOx concentration correspondence value calculated in the main process is output to the ECU 90 of the sensor control device 1 at predetermined intervals after it is determined that the concentration correspondence value included in the detection target gas can be stably detected in an output process performed independently of the main process. In the output process, it is determined whether the concentration correspondence value can be stably detected, depending on whether a predetermined time in which the $NO_x$ concentration correspondence value enters a predetermined range (for example, 0±5 ppm) elapses.

When the internal combustion engine (not shown) starts up and an instruction from the ECU 90 is input to the signal input and output unit 64, the CPU 61 acquires various conditions in which the main process is performed from the ROM 63 (S5). In S5, for example, a second time set for each gas sensor 10 is read. Then, the CPU 61 performs an activation process (S10 to S30). In the activation process, the CPU 61 starts electrification of the heater pattern 38 of the gas sensor 10 (S10). Specifically, the CPU 61 controls the heater drive circuit 59 so as to apply a constant voltage (for example, 12 V) to the heater pattern 38.

Then, the CPU 61 controls the Icp supply circuit 54 so as to start the supply of the current Icp to the Vs cell 3 (S15). The Vs cell 3 supplied with the current Icp pumps out oxygen from the first measuring chamber 23 to the reference oxygen chamber 29. When the detection element 11 is heated by the heater element 35 to lower the internal resistance of the Vs cell 3, the voltage Vs of the Vs cell 3 is slowly lowered.

Then, the CPU 61 determines whether the voltage Vs acquired from the Vs detection circuit 53 is equal to or less than a predetermined value Vth (S20). When it is determined that the voltage Vs is not equal to nor less than the predetermined value Vth (NO in S20), the CPU 61 waits until the voltage Vs becomes equal to or less than the predetermined value Vth. When it is determined that the voltage Vs is equal to or less than the predetermined value Vth (YES in S20), the CPU 61 starts to control the heater voltage Vh (S25). Specifically, the CPU 61 controls electrification of the heater element 35 through the use of the heater drive circuit 59 so that the internal resistance Rpvs of the Vs cell 3 reaches a target value. The target value is, for example, 300Ω, and the temperature of the Vs cell 3 is estimated to be about 750° C. when the internal resistance Rpvs is 300Ω.

Then, the CPU 61 determines whether the detection element 11 is activated (S30). Specifically, the CPU 61 determines whether the detection element 11 is activated depending on whether the internal resistance Rpvs of the Vs cell 3 reaches a threshold value. The internal resistance Rpvs of the Vs cell 3 is periodically calculated through a different process based on a variation of the voltage Vs acquired using the resistance detection circuit 55 and a table in which the variation of the voltage Vs is correlated with the internal resistance of the Vs cell 3. The threshold value is, for example, 350Ω, and the temperature of the Vs cell 3 is estimated to be about 650° C. when the internal resistance Rpvs is 350Ω. When the internal resistance Rpvs reaches the threshold value, the CPU 61 determines that the solid electrolytes 12, 13, and 14 reach a state exhibiting appropriate oxygen ion conductivity and the detection element 11 is activated.

When it is determined that the detection element 11 is not activated (NO in S30), the CPU 61 waits until the detection element 11 is activated. When it is determined that the detection element 11 is activated (YES in S30), the CPU 61 determines that the timing is an activation timing and starts up a first timer circuit not shown. The first timer circuit is configured to time out in a first time from the activation timing. The first time is, for example, 5 seconds. The CPU 61 determines whether the first time elapses after the first timer circuit starts up and the first timer circuit times out (S33). The CPU 61 continuously monitors the first timer circuit when it is determined that the first timer circuit does not time out (NO in S33). When it is determined that the first timer circuit times out (YES in S33), the CPU 61 determines that the elapse timing comes in, and drives the Ip1 drive circuit 52 to start to electrify the Ip1 cell 2 (S35). The process of S35 is a process of starting the concentration control at the elapse timing. That is, a process of adjusting the oxygen concentration of the exhaust gas introduced into the first measuring chamber 23 to a predetermined concentration C is started by electrification of the Ip1 cell 2.

Then, the CPU 61 performs the preliminary control process (S40 to S50). In the preliminary control process, the CPU 61 supplies current of a constant value to the Ip2 cell 4 for a constant second time individually set for each gas sensor 10 (S40). Specifically, the CPU 61 drives the constant current circuit 58 to supply the current Ip3 of a constant value to the Ip2 cell 4. The current Ip3 of a constant value is, for example, 10 μA. The Ip2 cell 4 is supplied with the current Ip3 and starts to pump out oxygen present in the second measuring chamber 30.

Then, the CPU 61 starts up a second timer circuit not shown (S45). The second timer circuit is configured to time out in a second time after the second timer circuit starts up. The second time is a value set for each gas sensor 10 and stored in the ROM 63 as described above. The second time is, for example, 20 seconds. Then, the CPU 61 determines whether the second time elapses after the second timer circuit starts up and the second timer circuit times out (S50). When it is determined that the second timer circuit does not time out (NO in S50), the CPU 61 continuously monitors the second timer circuit. When it is determined that the second timer circuit times out (YES in S50), the CPU 61 ends the preliminary control process. The CPU 61 determines that the start timing comes in and switches the control of the Ip2 cell 4 to the drive control (S55). The CPU 61 stops the driving of the constant current circuit 58 and drives the Vp2 application circuit 57 to switch the control state of the sensor control device 1 from the preliminary control to the drive control. Accordingly, in the drive control, an operation voltage Vp2 (for example, 450 mV) is applied to the Ip2 cell 4. In the drive control, the concentration control started in S35 is continuously performed.

Then, the CPU 61 acquires a value of the current Ip2 (more specifically, a value obtained by converting the current Ip2 into a voltage) detected by the Ip2 detection circuit 56 and stores the acquired value of the current Ip2 in the RAM 62 (S60). Then, the CPU 61 calculates the $NO_x$ concentration correspondence value and stores the calculated $NO_x$ concentration correspondence value in the RAM 62 (S70). The $NO_x$ concentration correspondence value is calculated, for example, by substituting the value of the current Ip2 for a predetermined calculation expression stored in the ROM 63. For example, the $NO_x$ concentration correspondence value corresponding to the value of the current Ip2 acquired in S60 is calculated, for example, by referring to the table in which the value of the current Ip2 is correlated with the $NO_x$ concentration correspondence value.

When it is determined that an end instruction is not input from the ECU 90 (NO in S80), the CPU 61 returns the process flow to S60. When it is determined that the end instruction is input from the ECU 90 (YES in S80), the CPU 61 ends the main process.

Evaluation Test

Figure 3:
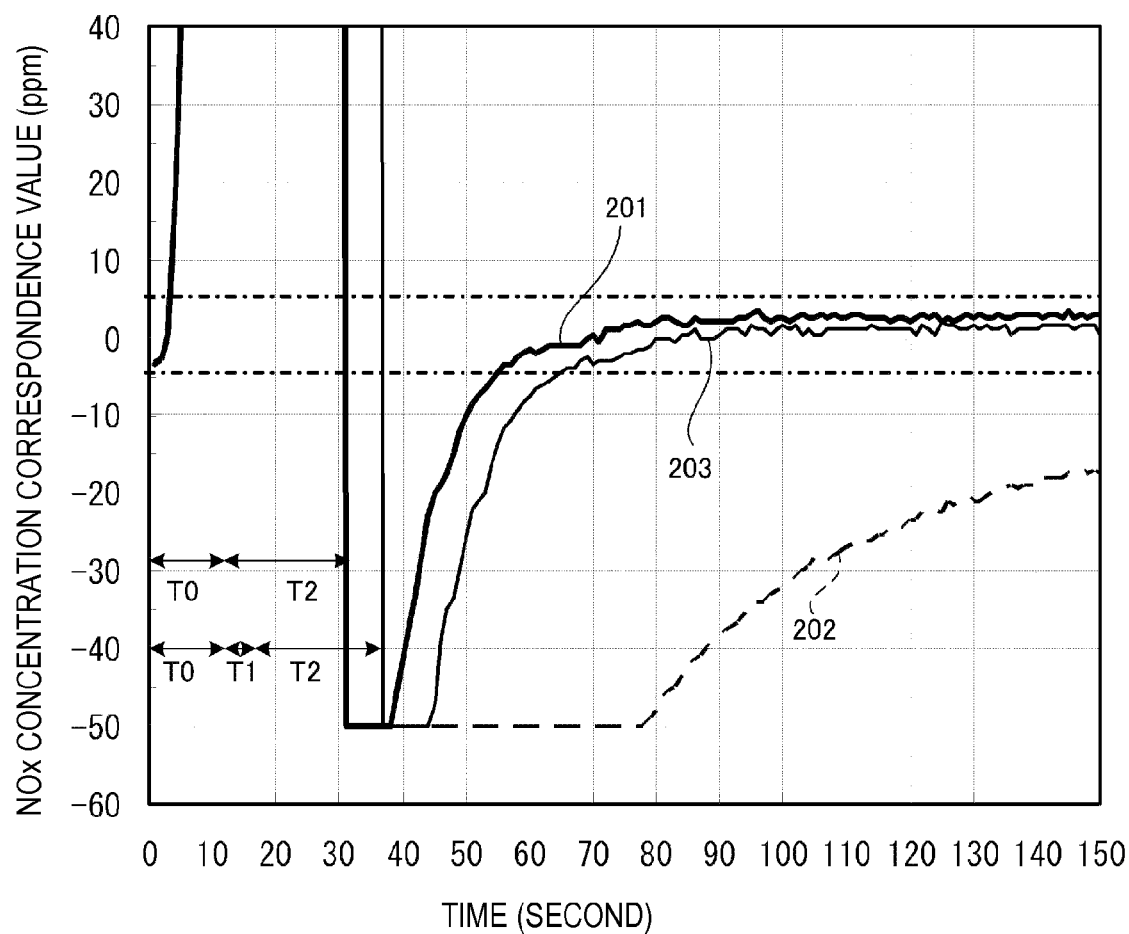
FIG. 3 is a graph illustrating a temporal variation of an NOx concentration correspondence value with a startup starting time of a gas sensor 10 to 0 (seconds) when the conventional preliminary control is performed using the gas sensor 10 having an unburned material not entered, when the conventional preliminary control is performed using a gas sensor 10 having an unburned material entered, and when the preliminary control according to the embodiment is performed using a gas sensor 10 having an unburned material entered.

An evaluation test for checking whether the concentration of a specific gas can be stably and early detected was performed, even when the main process of the first embodiment was performed and an unburned material enters the gas sensor 10. Specifically, in a sensor control device 1 including a gas sensor 10 having the same configuration, temporal variations of the NO concentration correspondence values obtained under different Conditions 1 to 3 were compared. Condition 1 is a condition in which the preliminary control is performed using the conventional method in a state where an unburned material has not entered the gas sensor 10. Condition 2 is a condition in which the preliminary control is performed using the conventional method in a state where an unburned material has entered the gas sensor 10. Condition 3 is a condition in which the preliminary control is performed using the main process according to the first embodiment in a state where an unburned material has entered the gas sensor 10. In the present evaluation, the gas sensor 10 in which a known baking inhibitor was applied to the outer circumference of a housing was left in an air-tightly closed vessel containing the atmospheric air of 80° C. for 100 hours, whereby an organic gas (unburned material) was generated from the baking inhibitor and the state where the unburned material has entered the gas sensor 10 (second measuring chamber 30) was obtained. The detection target gas was a gas including 0 ppm of $NO_x$, 20% of $O_2$, and 4% of $H_2O$, and a balance of N2. The temperature of the detection target gas was 150° C. In FIG. 3, the horizontal axis represents the elapsed time (unit: second) from the startup timing and the vertical axis represents the $NO_x$ concentration correspondence value (unit: ppm).

The temporal variations of the $NO_x$ concentration correspondence values of Conditions 1 to 3 are indicated by patterns 201 to 203, respectively. In Conditions 1 and 2, after the gas sensor 10 is started up, the gas sensor 10 is activated in a time T0 (12 seconds) after the electrification of the heater pattern 38 is started, and the preliminary control is started from the activation timing. In the preliminary control, constant current (10 µA) is supplied to the Ip2 cell 4 for the second time T2 (20 seconds) set for each gas sensor 10, and then the preliminary control is switched to the drive control. On the other hand, in Condition 3, the preliminary control is started from the elapse timing at which the first time T1 (5 seconds) has elapsed from the activation timing.

In Conditions 1 to 3, oxygen present in the second measuring chamber 30 is forcibly pumped out to the reference oxygen chamber 29 through the use of the preliminary control. In Condition 1, the oxygen concentration in the second measuring chamber 30 has a value close to the oxygen concentration of the atmospheric air just after the activation process. In Conditions 2 and 3, since the unburned material is oxidized through the activation process, it is assumed that the oxygen concentration in the second measuring chamber 30 has a value lower than the oxygen concentration of the atmospheric air. In Conditions 1 to 3, oxygen present in the second measuring chamber 30 is forcibly pumped out to the reference oxygen chamber 29 through the use of the preliminary control. Just after the preliminary control is switched to the drive control, the second measuring chamber 30 is in a low-oxygen state (rich atmosphere) in which the oxygen concentration is lower than a reference concentration. As described above, the oxygen concentration in the second measuring chamber 30 at the time of performing the drive control is set in advance to a concentration as a reference (reference concentration) with a voltage of Vp2=450 mV. Accordingly, just after the preliminary control is switched to the drive control, the Ip2 cell 4 operates to return oxygen from the reference oxygen chamber 29 to the second measuring chamber 30 so that the oxygen concentration in the second measuring chamber 30 becomes the reference concentration. Accordingly, the output of the $NO_x$ concentration correspondence value rises from the minus side after the preliminary control as shown in FIG. 3.

As shown in FIG. 3, in Condition 1 indicated by pattern 201, the $NO_x$ concentration correspondence value rose from the minus side after the start timing, rapidly increased up to 30 seconds (62 seconds from the startup timing) from the start timing, and slowly increased thereafter. The $NO_x$ concentration correspondence value was in a range of 0±5 ppm after 23 seconds passed from the start timing (55 seconds from the startup timing).

In Condition 2 indicated by pattern 202, the $NO_x$ concentration correspondence value rose from the minus side after the start timing and had a value outside the detection range up to 46 seconds (78 seconds from the startup timing) from the start timing, and the $NO_x$ concentration correspondence value slowly increased after 47 seconds (79 seconds from the startup timing) from the start timing. In Condition 2, 200 seconds or more from the start up timing was necessary until the $NO_x$ concentration correspondence value was in the range of 0±5 ppm. In Condition 2, it is assumed that the second measuring chamber 30 is in a low-oxygen state (rich atmosphere) in which the oxygen concentration is lower than a predetermined low concentration due to the influence of the unburned material entering the gas sensor 10 at the activation timing. Accordingly, compared with Condition 1, time is taken for returning oxygen from the reference oxygen chamber 29 to the second measuring chamber 30 after the preliminary control ends.

In Condition 3 indicated by pattern 203, the $NO_x$ concentration correspondence value rose from the minus side after the start timing, rapidly increased (70 seconds from the startup timing) from the start timing for 33 seconds, and slowly increased thereafter. After 27 seconds elapsed from the start timing (after 64 seconds elapsed from the startup timing), the $NO_x$ concentration correspondence value was in the range of 0±5 ppm.

In Condition 3, similarly to Condition 2, it is assumed that the second measuring chamber 30 is in a low-oxygen state (rich atmosphere) in which the oxygen concentration is lower than a predetermined low concentration due to the influence of the unburned material entering the gas sensor 10 at the activation timing. However, in Condition 3, the concentration control and the preliminary control are started from the elapse timing at which the first time (5 seconds) elapses from the activation timing. Accordingly, the atmosphere of the second measuring chamber is replaced with the atmosphere around the gas sensor 10 under the condition in which the gas sensor 10 is activated. Therefore, the time necessary for returning oxygen from the reference oxygen chamber 29 to the second measuring chamber 30 after the preliminary control ends is the same time as in Condition 1. As a result, the startup time in Condition 3 is 64 seconds, which is a half or less of the startup time (200 seconds or more) in Condition 2. Although not shown in the drawing, the temporal variation of the same $NO_x$ concentration correspondence value was acquired by performing the preliminary control through the use of the main process according to the first embodiment in a state where an unburned material did not enter the gas sensor 10, and substantially the same pattern as in Condition 3 was obtained. It was confirmed from the evaluation test that it was possible to stably and early detect the concentration of a specific gas without depending on whether an unburned material entered the gas sensor 10 when the main process according to the embodiment was applied to the sensor control device 1.

The following advantages are obtained from the sensor control device 1 according to the first embodiment described in detail above. Since the first time is set to be shorter than the second time, it is possible to stably and early detect the concentration of a specific gas without depending on whether an unburned material enters the gas sensor 10 while suppressing the ratio of the first time to the startup time to be low. In the sensor control device 1, constant current is supplied to the Ip2 cell 4 for the constant second time determined for each gas sensor 10 as the preliminary control. The amount of oxygen pumped out by the Ip2 cell 4 is proportional to the value of current flowing between a pair of electrodes 27 and 28 of the Ip2 cell 4. Accordingly, in the sensor control device 1, the oxygen concentration in the second measuring chamber 30 at the time of ending the preliminary control has substantially the same value for the same gas sensor 10, without depending on the $H_2O$ concentration of the detection target gas. Therefore, the sensor control device 1 can reduce the deviation of the startup time between the detection processes performed in the same gas sensor 10 in consideration of the deviation in output characteristics between the gas sensors 10.

Regarding the main process of the first embodiment, the CPU 61 of the controller 5 performs the main process. On the contrary, when the gas sensor include a controller, the controller of the gas sensor and a controller disposed independently of the gas sensor may perform the main process in cooperation with each other. Hereinafter, a second embodiment in which the controller of the gas sensor and the controller disposed independently of the gas sensor perform the process in cooperation with each other will be described below with reference to FIGS. 4 to 6.

Figure 4:
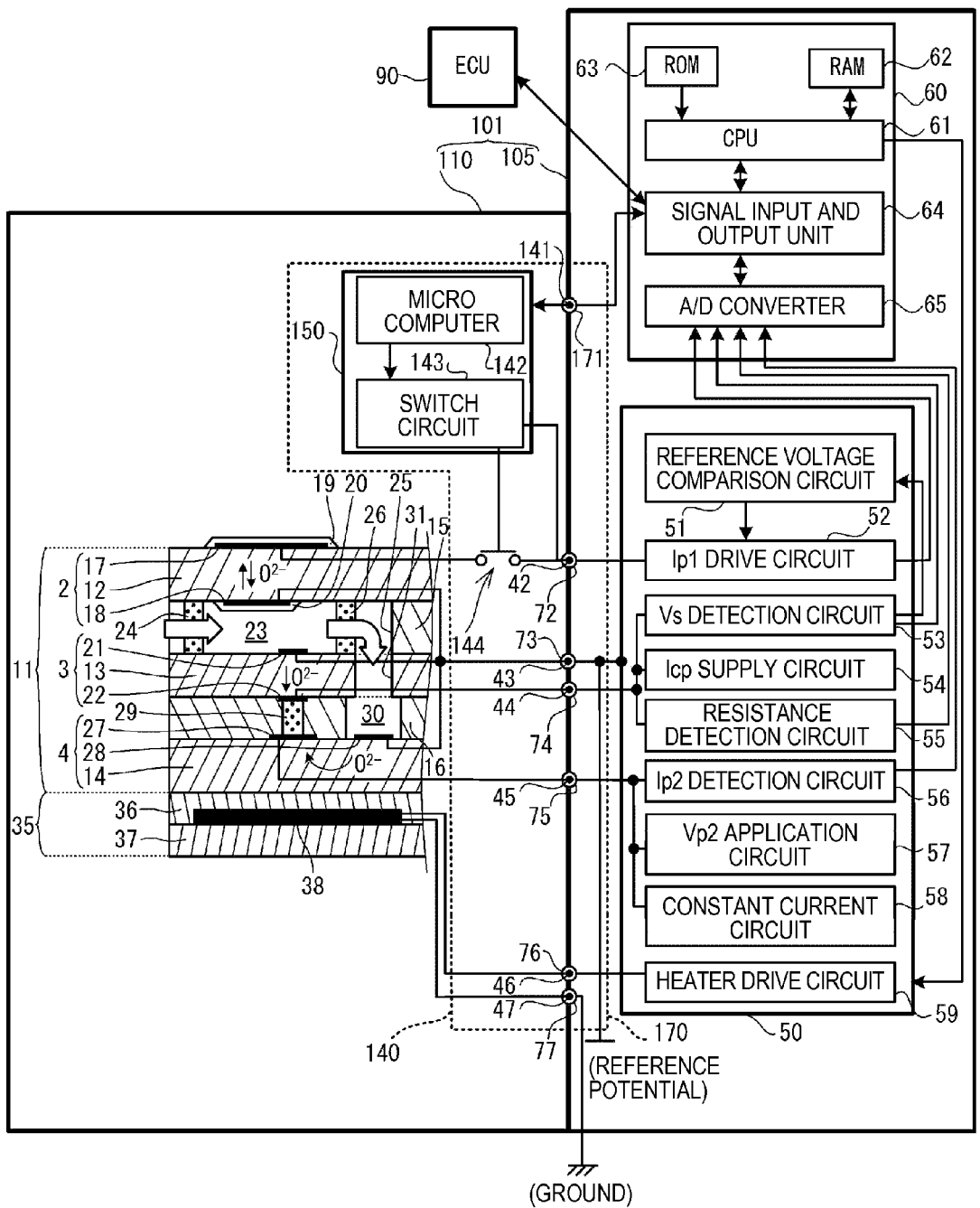
FIG. 4 is a conceptual diagram of a sensor control device 101 according to a second embodiment.

First, the configuration of a sensor control device 101 according to the second embodiment will be described with reference to FIG. 4. In FIG. 4, the same constituents as included in the sensor control device 1 according to the first embodiment shown in FIG. 1 are referenced by the same reference signs. In the following description, the same constituents as included in the sensor control device 1 according to the first embodiment will not be described. As shown in FIG. 4, the sensor control device 101 according to the second embodiment includes a controller 105 and a gas sensor 110. The controller 105 is different from that of the sensor control device 1 according to the first embodiment in the configuration of the connector section 170. The connection section 170 includes a terminal 171 in addition to the same terminals 72 to 77 as in the first embodiment. The terminal 171 is electrically connected to the signal input and output unit 64 via a line.

The gas sensor 110 is different from that of the sensor control device 1 according to the first embodiment in the configuration of the connector section 140. The connector section 140 includes a controller 150, a terminal 141, and a switch 144 in addition to the same terminals 42 to 47 as in the first embodiment. The controller 150 includes a micro computer 142 (hereinafter, referred to as "microcomputer 142") and a switch circuit 143. Although not shown in the drawing, the microcomputer 142 is a computing device including a CPU, a ROM, a RAM, an A/D converter, and a signal input and output unit, which are known well. The switch circuit 143 controls the switching of a switch 144. The switch 144 is controlled by the switch circuit 143 so as to switch opening and closing of a path through which the current Ip1 supplied from the Ip1 drive circuit 52 flows. The terminal 141 is electrically connected to the controller 150 via a lead line. When the connector section 170 is connected to the connector section 140, the terminals 72 to 77 and the terminal 171 are connected to the terminals 42 to 47 and the terminal 141, respectively.

The processes performed by the sensor control device 101 according to the second embodiment will be described below in brief. The controller 105 drives the Ip1 drive circuit 52 from the activation timing to start the supply of current Ip1 (S35) and then outputs a supply start signal to the controller 150, by performing the main process shown in FIG. 6. The supply start signal is a signal for notifying the controller 150 of the start of the supply of current Ip1. Thereafter, the controller 105 performs a process of waiting until the value of a flag set by the gas sensor 110 is 1 (S38). On the other hand, the controller 150 of the gas sensor 110 performs a switching process shown in FIG. 5 to set the flag to 0 (s100), and then performs a closing process of closing the path through which the current Ip1 flows until the first time elapses after the supply start signal is received (S110 and S115). When the closing process is finished (YES in S115, S120), the controller 150 sets the flag to 1 (S125). Through the use of these processes, the sensor control device 101 starts the concentration control (the process in a two-dot chained line 194 in FIG. 6) from the elapse timing and performs the preliminary control (the process in a two-dot chained line 92 in FIG. 6) in a period between the elapse timing and the start timing.

Figure 5:
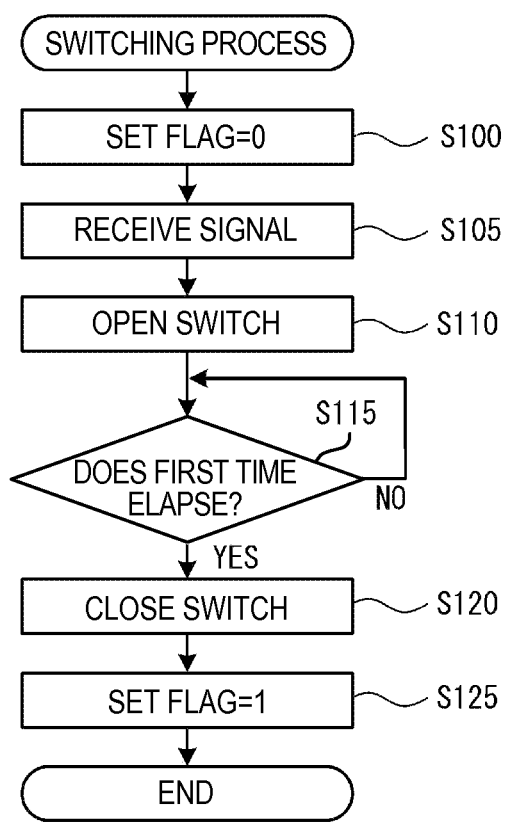
FIG. 5 is a flowchart illustrating a switching process which is performed by a gas sensor 110 according to the second embodiment.

The switching process performed by the gas sensor 11 according to the second embodiment will be described below with reference to FIG. 5. The switching process is performed by the controller 150 in response to an instruction from the micro computer of the controller 105 when the internal combustion engine (not shown). As shown in FIG. 5, in the switching process, the controller 150 first sets the flag to 0 (S100). The flag is set to determine whether the closing process of closing the path through which the current Ip1 flows is finished. When the flag is 0, the flag represents that the closing process is not finished. When the flag is 1, the flag represents that the closing process is finished. The micro computer 142 outputs the setting of the flag to the signal input and output unit 64 of the controller 105. Then, when the supply of the current Ip1 is started by the controller 105, the micro computer 142 receives the supply start signal from the signal input and output unit 64 of the controller 105 (S105). Then, the micro computer 142 outputs an instruction to open the switch 144 to the switch circuit 143 and starts the closing process (S110) based on the supply start signal received from the controller 105. The switch circuit 143 opens the switch 144 in response to the output instruction. When the switch 144 is opened, the current Ip1 is not supplied to the Ip1 cell 2. The micro computer 142 waits until the first time elapses after the switch circuit 143 opens the switch 44 (NO in S115), and gives an instruction to close the switch 144 to the switch circuit 143 when the first time elapses after the switch circuit 143 opens the switch 144 (YES in S115) (S120). The switch circuit 143 closes the switch 144 in response to the output instruction. Through the processes of S110 to S120, the switch circuit 143 connects the switch 144 to a line in which the current Ip1 flows in the first time after the closing process is started. Then, since the closing process is finished, the micro computer 142 sets the flag to 1 and outputs the setting of the flag to the signal input and output unit 64 (S125). The switching process is finished in this way.

Figure 6:
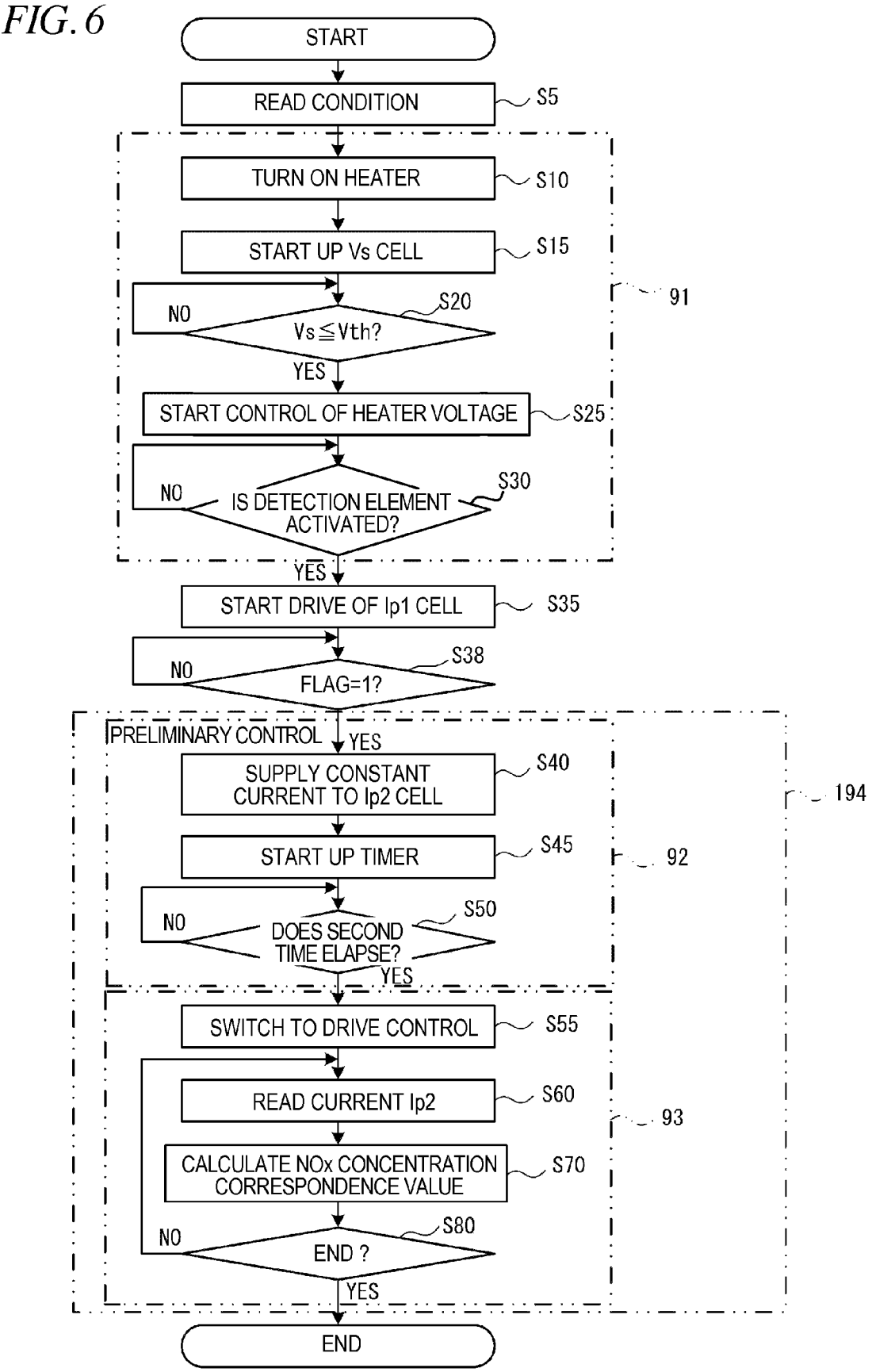
FIG. 6 is a flowchart illustrating the flow of main process which is performed by a controller 105 according to the second embodiment.

The main process which is performed by the controller 105 according to the second embodiment will be described below with reference to FIG. 6. The main process is performed by the CPU 61 in response to an instruction from the ECU 90 when the internal combustion engine (not shown) is started up. In FIG. 6, the same processes as in the main process according to the first embodiment shown in FIG. 2 are referenced by the same step numerals. As shown in FIG. 6, the main process according to the second embodiment is different from the main process according to the first embodiment shown in FIG. 2, in that the process of S33 is not performed and the process of S38 is performed between S35 and S40 and in the process of S35. The same processes as in the first embodiment will not be described and the processes of S35 and S38 which are different from the main process according to the first embodiment will be described below.

In S35, the CPU 61 drives the Ip1 drive circuit 52 and starts the electrification of the Ip1 cell 2. The CPU 61 outputs the supply start signal to the controller 150. In S38, the CPU 61 determines whether the flag is 1. The flag is set by the gas sensor 110 in the switching process. The CPU 61 waits until it is determined that the flag is 1 (NO in S38), and performs the same process of S40 and processes subsequent thereto as in the first embodiment when it is determined that the flag is 1 (YES in S38).

In the sensor control device 101 according to the second embodiment, the controller 105 drives the Ip1 drive circuit 52 at the activation timing. On the other hand, the switch circuit 143 of the gas sensor 110 controls the opening and closing of the switch 144 so as to start the concentration control from the elapse timing. As a result, in the sensor control device 101 according to the second embodiment, the same process as the main process in the sensor control device 1 according to the first embodiment is performed. Therefore, it is possible to achieve the same advantages as in the sensor control device 1 according to the first embodiment.

The present invention is not limited to the first and second embodiments, but may be modified in various forms without departing from the concept of the present invention. For example, modifications described in (1) to (7) may be appropriately made.

(1) While the temperature of the detection element 11 is detected based on the internal resistance of the Vs cell 3 in the above-mentioned embodiments, the temperature of the detection element 11 may be detected, for example, based on the internal resistance of at least one of the Ip1 cell 2 and the Ip2 cell 4 instead of the Vs cell 3. The temperature of the detection element 11 may be detected based on the resistance value of the heater pattern 38 constituting the heater element 35.

(2) While the $NO_x$ sensor detecting the $NO_x$ concentration is exemplified in the above-mentioned embodiments, the sensor control device according to the first aspect can be applied to various gas sensors (for example, an oxygen sensor) constructed using a solid electrolyte.

(3) The configuration of the sensor control device can be appropriately modified. For example, the configuration of the drive circuit unit of the controller 5 (105) may be appropriately modified. For example, the controller 5 and the gas sensor 10 may be configured as a unified body so as not to be attached and detached each other. For example, the sensor control device according to this aspect may be applied to a gas sensor having an air introduction hole instead of the reference oxygen chamber 29.

(4) The performance conditions of the preliminary control can be appropriately modified. For example, as described in the above-mentioned embodiments, constant current may be supplied for a constant time in the preliminary condition. In this case, as the performance conditions of the preliminary control for each gas sensor 10, for example, a combination of the value of the constant current in the preliminary control, the electrification time, and the condition selected from the target heating temperature of the gas sensor 10 may be set or the same control condition for the gas sensors 10 having the same configuration may be set. When the sensor control device is used in an environment not affected by the $H_2O$ concentration or the like, a constant voltage larger than the operation voltage may be supplied for a constant time as the preliminary control.

(5) The main process in the above-mentioned embodiments can be appropriately modified. For example, the pattern obtained through the main process according to the embodiments is the same pattern for every performance of the main process. Accordingly, a process of correcting the $NO_x$ concentration correspondence value using correction data in the pattern obtained through the main process according to the embodiments may be performed. For example, the $NO_x$ concentration correspondence value calculated in S70 of FIG. 2 has only to be a value indicating the concentration of a specific gas in the detection target gas. For example, the $NO_x$ concentration correspondence value may be value obtained by converting the analog output based on the current value of the Ip2 cell 4 into a digital value. For example, the preliminary control has only to be performed in at least a partial period between the elapse timing and the start timing. Specifically, in the above-mentioned embodiments, the concentration control and the preliminary control are started substantially at the same time at the elapse timing, but the preliminary control may be performed after the concentration control is started.

(6) It is preferable that the first time be shorter than the second time, from the viewpoint of shortening the startup time, but the first time may be equal to or more than the second time when stability for early enabling the detection of the concentration of a specific gas increases by extending the first time or the like.

Figure 2:
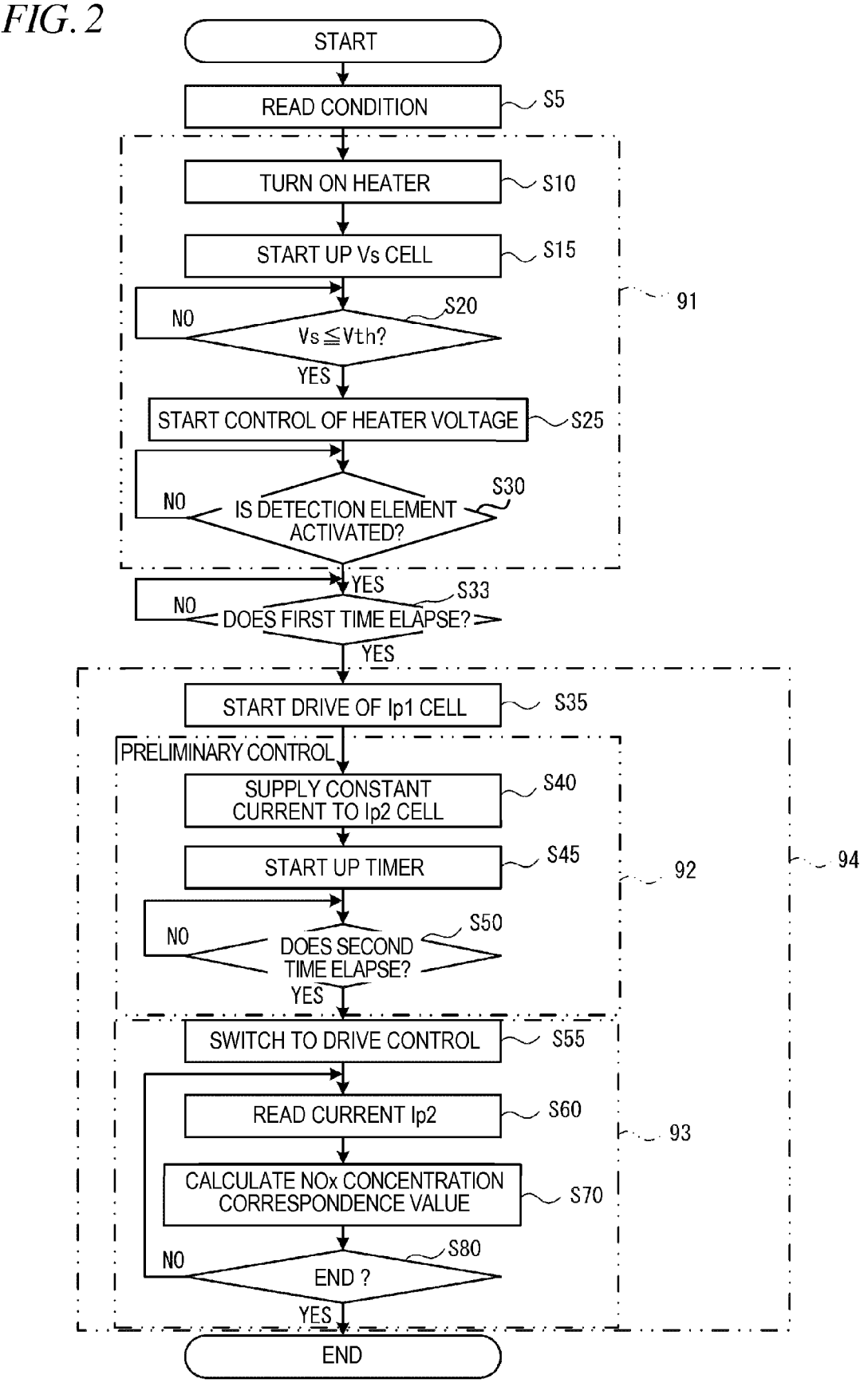
FIG. 2 is a flowchart illustrating the flow of a main process which is performed by a controller 5 according to the first embodiment.

(7) The steps of the main process shown in FIGS. 2 and 6 are not performed by only the CPU 61, but all or a part thereof may be performed by another electronic device (for example, ASIC). The steps of the main process may be distributed and performed by plural electronic devices (for example, plural CPUs). The steps of the main process shown in FIGS. 2 and 6 and the switching process shown in FIG. 5 can be subjected to change of the order, omission of some steps, and addition of steps, if necessary.

What is claimed is:

1. A sensor control method for controlling a gas sensor including: a first measuring chamber into which a detection target gas is to be introduced; a first oxygen pump cell that includes a first solid electrolyte layer and a pair of first electrodes which are disposed inside and outside the first measuring chamber, respectively; a second measuring chamber communicating with the first measuring chamber; and a second oxygen pump cell that includes a second solid electrolyte layer and a pair of second electrodes which are disposed inside and outside the second measuring chamber, respectively, the sensor control method comprising:

performing a concentration control of adjusting an oxygen concentration in the detection target gas introduced into the first measuring chamber to a predetermined value through electrification of the first oxygen pump cell;

performing a drive control of applying an operation voltage to the second oxygen pump cell;

calculating a concentration correspondence value indicating a concentration of a specific gas based on the magnitude of current flowing in the second oxygen pump cell to which the operation voltage has been applied;

determining whether the gas sensor is activated;

performing a preliminary control of lowering the oxygen concentration in the second measuring chamber before starting the drive control;

determining whether a first as elapsed from an activation timing at which the gas sensor is determined to be activated;

performing the concentration control at an elapse timing which elapses by the first time; and performing the preliminary control in at least a partial period between the elapse timing and a start timing at which the drive control is started.

2. A sensor control device comprising:

a gas sensor including:

a first measuring chamber into which a detection target gas is to be introduced;

a first oxygen pump cell that includes a first solid electrolyte layer and a pair of first electrodes which are disposed inside and outside the first measuring chamber, respectively;

a second measuring chamber communicating with the first measuring chamber; and a second oxygen pump cell that includes a second solid electrolyte layer and a pair of second electrodes which are disposed inside and outside the second measuring chamber, respectively; and a controller configured to:

perform a concentration control of adjusting an oxygen concentration in the detection target gas introduced into the first measuring chamber to a predetermined value through electrification of the first oxygen pump cell;

perform a drive control of applying an operation voltage to the second oxygen pump cell;

calculate a concentration correspondence value indicating a concentration of a specific gas based on the magnitude of current flowing in the second oxygen pump cell to which the operation voltage has been applied;

determine whether the gas sensor is activated;

perform a preliminary control of lowering the oxygen concentration in the second measuring chamber before starting the drive control;

determine whether a first time has elapsed from an activation timing at which the gas sensor is determined to be activated;

perform the concentration control at an elapse timing which elapses by the first time; and perform the preliminary control in at least a partial period between the elapse timing and a start timing at which the drive control is started.

3. The sensor control device according to claim 2, wherein the controller is configured to perform the preliminary control by supplying constant current to the second oxygen pump cell for a constant second time to control an amount of oxygen to be pumped out form the second measuring chamber to the outside of the second measuring chamber so as to be constant.

4. The sensor control device according to claim 3, wherein the first time is shorter than the second time.

5. A non-transitory computer readable recording medium storing a program, for a sensor control device including: a first measuring chamber into which a detection target gas is to be introduced; a first oxygen pump cell that includes a first solid electrolyte layer and a pair of first electrodes which are disposed inside and outside the first measuring chamber, respectively; a second measuring chamber communicating with the first measuring chamber; and a second oxygen pump cell that includes a second solid electrolyte layer and a pair of second electrodes which are disposed inside and outside the second measuring chamber, respectively, the program when executed by a processor causing the sensor control device to:

perform a concentration control of adjusting an oxygen concentration in the detection target gas introduced into the first measuring chamber to a predetermined value through electrification of the first oxygen pump cell;

perform a drive control of applying an operation voltage to the second oxygen pump cell;

calculate a concentration correspondence value indicating a concentration of a specific gas based on the magnitude of current flowing in the second oxygen pump cell to which the operation voltage has been applied;

determine whether the gas sensor is activated;

perform a preliminary control of lowering the oxygen concentration in the second measuring chamber before starting the drive control;

determine whether a first time has elapsed from an activation timing at which the gas sensor is determined to be activated;

perform the concentration control at an elapse timing which elapses by the first time; and perform the preliminary control in at least a partial period between the elapse timing and a start timing at which the drive control is started.

* * * * *